United States Patent [19]

Hedaya et al.

[11] 4,145,504

[45] Mar. 20, 1979

[54] HIGH TEMPERATURE CARBORANE-SILOXANE ELASTOMERS INTERMEDIATE POLYMERIC PRODUCTS AND PROCESS FOR PREPARATION

[75] Inventors: Eddie Hedaya, White Plains, N.Y.; James H. Kawakami, Piscataway; George T. Kwiatkowski, Greenbrook, both of N.J.

[73] Assignee: Union Carbide Corporation, New York, N.Y.

[21] Appl. No.: 770,509

[22] Filed: Feb. 22, 1977

Related U.S. Application Data

[63] Continuation-in-part of Ser. No. 588,850, Jun. 20, 1975, abandoned, which is a continuation of Ser. No. 500,473, Aug. 26, 1974, abandoned, which is a continuation of Ser. No. 382,278, Jul. 24, 1973, abandoned.

[51] Int. Cl.$^2$ ............................................. C08G 77/04
[52] U.S. Cl. .................................... 528/5; 260/37 SB; 528/30; 528/32; 528/34; 528/41; 528/43

[58] Field of Search ..................... 260/46.5 G, 46.5 E, 260/37 SB

[56] References Cited

U.S. PATENT DOCUMENTS

| | | | |
|---|---|---|---|
| 3,388,092 | 6/1968 | Heying et al. | 260/46.5 E |
| 3,661,847 | 5/1972 | Chapman | 260/46.5 E |
| 3,733,298 | 5/1973 | Knollmueller | 260/46.5 E |

*Primary Examiner*—Melvyn I. Marquis
*Attorney, Agent, or Firm*—William Raymond Moran

[57] ABSTRACT

Carborane-siloxane polymers are conveniently prepared by the polymerization of a carborane disilanol and either a silyl diamine, a ureido-silane, or a silyl dicarbamate. The resulting linear polymers are characterized by relatively high molecular weights and are elastomeric in nature. These gumstocks are compounded with suitable fillers and additives and fabricated into cured elastomeric articles. The carborane-siloxane elastomers exhibit excellent high temperature properties which render them especially useful for a wide variety of applications, such as gaskets, seals, wire and cable insulation and the like.

18 Claims, No Drawings

HIGH TEMPERATURE CARBORANE-SILOXANE ELASTOMERS INTERMEDIATE POLYMERIC PRODUCTS AND PROCESS FOR PREPARATION

This application is a continuation-in-part of application Ser. No. 588,850 filed June 20, 1975. Application Ser. No. 588,850 is a continuation of application Ser. No. 500,473 filed Aug. 26, 1974 which is a continuation of application Ser. No. 382,278 filed July 24, 1973, all of which have been abandoned.

This invention relates in general to carborane-siloxane elastomers, intermediate polymeric products, and to a process for their preparation. In one aspect this invention is directed to carborane-siloxane elastomers having excellent high temperature properties and chemical stability. In a further aspect this invention relates to a process for the preparation of linear carborane-siloxane polymers and polymeric gumstock.

Important requirements exist in industry for elastomeric materials which are fuel resistant, stable for extended periods of time at temperatures in excess of 500° F. and possess good mechanical properties. New high temperature elastomers are in demand because currently available products such as the silicone and fluorocarbon rubbers for the most part do not meet these and other requirements.

Materials based on triazines or polyimides have shown promise in laboratory evaluations up to 600° F., however, they have poor low temperature flexibility and limited hydrolytic stability. In recent years a class of carborane-siloxane polymers has become available which are said to perform satisfactorily at high temperatures. The identity and method of preparation are set forth in an article entitled "Carboranesiloxane Polymers" by H. A. Schroeder appearing in Rubber Age, February 1969 (see also U.S. Pat. No. 3,689,455). However, these so-called Dexsil[(1)] polymers have found only limited applications owing to fabrication difficulties and poor mechanical properties which results from their crosslinking during synthesis. These problems are inherent in the ferric chloride catalyzed preparation of Dexsil 200 materials; the ferric chloride causes crosslinking to occur during polymerization which results in a difficult to fabricate insoluble resin. The use of ferric chloride has other disadvantages, for example, it does not permit one to introduce solvent resistant groups such as trifluoropropyl or vulcanization moieties such as vinylsiloxane. Fluorocarbon elastomers have service lives of several hundred hours at 400° F., but have poor low temperature flexibility (about −20° F. capability). Fluorosilicones have a broad temperature capability (−75° to 450° F.) but have poor tensile strengths and low abrasion resistance.

[(1)] Silicone carborane elastomers produced by the Olin Corporation.

It was therefore evident that carborane-siloxane elastomers, which possess unique high temperature properties, have the greatest potential for advanced aerospace, military, and electronic applications if the fuel resistance and poor mechanical properties problems were solved. Since the ferric chloride polymerization was related to the above deficiencies, new polymerization techniques were needed which would yield linear high molecular weight polymers (better mechanical properties) and which would allow the incorporation of solvent resistant groups and vinyl moieties which can be vulcanized using standard silicone rubber technology. In addition, it was important to reduce crystallinity in these carborane-siloxanes to improve elastomeric properties such as elongations and to extend the continuous performance temperature range.

In order to circumvent these problems, a new polymerization process has now been developed based on a silanol-silylamine, silanol-ureido-silane or silanol-silylcarbamate condensation reaction to produce a linear, soluble polymer which greatly simplifies compounding and fabrication into high performance elastomeric composites and permits the introduction of a wide variety of groups.

For example, the process of this invention permits one to incorporate into the polymer trifluoropropyl groups for increasing solvent resistance, phenyl groups to increase thermo-oxidative stability and decrease crystallinity and vinyl groups for the vulcanization step. It is therefore evident that the process of this invention provides a different polymeric product possessing outstanding properties not found in the currently available carborane-siloxane polymers.

Accordingly, one or more of the following objects will be achieved by the practice of this invention. It is an object of this invention to provide carbonane-siloxane lastomers. Another object of this invention is to provide carbonate-siloxane elastomers which are characterized by relatively high molecular weights. A further object of this invention is to provide carborane-siloxane elastomers which are characterized by excellent high temperature properties, fuel resistance, and excellent mechanical properties which render them useful for a wide variety of applications. Another object of this invention is to provide certain intermediate products formed in the process, for subsequent conversion into elastomers. A further object is to prepare high molecular weight linear carborane-siloxane polymers. Another object is to provide a process for the preparation of linear, soluble polymers which are relatively easy to compound and fabricate into elastomeric articles and permits the introduction of solvent resistant groups. These and other objects will readily become apparent to those skilled in the art in the light of the teachings herein set forth.

In its broad aspect, this invention is directed to carborane-siloxane elastomers, intermediate products and to a process for their preparation. As previously indicated, the elastomers prepared by the process of this invention exhibit high temperature properties which render them particularly useful for a wide variety of applications. For example, the elastomers are useful in the fabrication of gaskets, seals, wire and cable insulation and the like.

In general, the invention is comprised of several embodiments. The first is directed to linear carborane-siloxane polymers formed by the condensation of silyl diamines or α,ω-diaminosiloanes with carborane disilanols. In a second embodiment, linear polymers are also prepared by the condensation of ureido-silanes or α,ω-ureido-siloxanes with carborane disilanols. In a further embodiment, carborane disilanols can be condensed with silyl biscarbamates or α,ω-carbamoylsiloxanes to form carborane siloxane polymers. Finally, the polymers can be fabricated into the carborane-siloxane elastomers by techniques known in the art.

In the first embodiment, the process comprises the steps of contacting disubstituted silyl amines or α,ω-diaminosiloxanes with carborane disilanols, in accordance with the following equation, to provide linear carborane-siloxane polymers having molecular weights of from about 5,000 up to about 150,000 and higher:

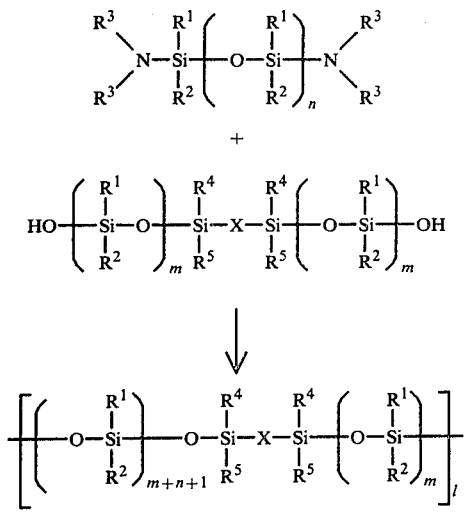

+

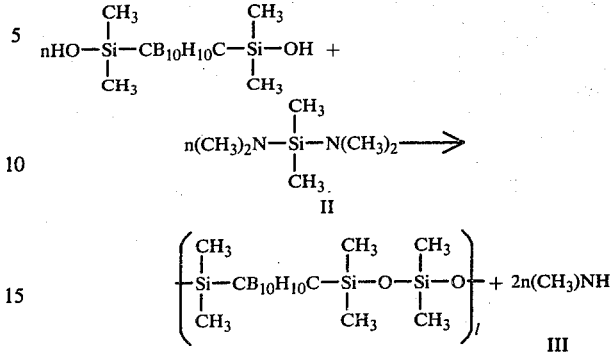

wherein:
(1) $R^1$ and $R^2$ individually represent hydrogen, or groups containing up to 14 carbon atoms and selected from the group consisting of alkyl, alkenyl, cycloalkyl, aryl, alkaryl, aralkyl, alkoxyaryl, haloalkyl, haloaryl, cyanoalkyl, morpholinyl, and pyridinyl;
(2) $R^3$ represents hydrogen, or groups containing up to 14 carbon atoms and selected from the group consisting of alkyl, alkenyl, cycloalkyl, aryl, alkaryl, aralkyl, alkoxyaryl, haloaryl, cyanoalkyl, morpholinyl and pyridinyl; and wherein 2 $R^3$s, can when taken together contain up to 6 carbon atoms and represent alkylene, dialkylene amine or alkylsubstituted dialkylene amine;
(3) $R^4$ and $R^5$ individually represent hydrogen or groups containing up to 14 carbon atoms and selected from the group consisting of alkyl, alkenyl, aryl, alkaryl, aralkyl, alkoxyalkyl, haloalkyl and haloaryl;
(4) X represents 1,7-decacarborane, 1,12-decacarborane, 1,10-octacarborane, 1,6-octacarborane, 2,4pentacarborane, 1,6-tetracarborane, 9-alkyl-1,7-decacarborane, 9,10-dialkyl-1,7-decacarborane, 2-alkyl-1,12-decacarborane, 2-alkyl-1,10-octacarborane, 8-alkyl-1,6-octacarborane, decachloro-1,7-decacarborane, decachloro-1,12-decacarborane, decachlorio-1,12-decacarborane, octachloro-1,10-octacarborane, decafluoro-1,7-decacarborane, decafluoro-1,12-decacarborante, octafluoro-1,10-octacarborane, or mixtures thereof, and
(5) m and n individually have a value of from 0 to 4 and more preferably from 0 to 2, and l has a value such that molecular weight of the polymer is from about 5,000 to about 150,000 and higher.

Illustrative of the R groups as hereinbefore defined are such groups as methyl, ethyl, n-propyl, n-butyl, n-pentyl, n-hexyl, n-butenyl, n-hexenyl, cyclopentyl, cyclohexyl, phenyl, benzyl, o-m-, or p-chlorophenyl, o-,m- or p-methylphenyl, o-,m-, or p-methoxyphenyl, 3,3,3-trifluoro-propyl, cyanomethyl, morpholinyl, pyridenyl and the like. The R groups need not be the same in any one polymeric claim. Particularly preferred are groups containing up to 7 carbon atoms.

Illustrative of a specific condensation reaction employing a silyl diamine is the reaction of carborane disilanol (I) $B_{10}H_{10}C_2$ $(SiMe_2OH)_2$, and silyl diamine (II) $SiMe_2$ $(Me_2N)_2$.

$$nHO-\underset{\underset{CH_3}{|}}{\overset{\overset{CH_3}{|}}{Si}}-CB_{10}H_{10}C-\underset{\underset{CH_3}{|}}{\overset{\overset{CH_3}{|}}{Si}}-OH +$$

$$n(CH_3)_2N-\underset{\underset{CH_3}{|}}{\overset{\overset{CH_3}{|}}{Si}}-N(CH_3)_2 \longrightarrow$$

II $$\left(\underset{\underset{CH_3}{|}}{\overset{\overset{CH_3}{|}}{Si}}-CB_{10}H_{10}C-\underset{\underset{CH_3}{|}}{\overset{\overset{CH_3}{|}}{Si}}-O-\underset{\underset{CH_3}{|}}{\overset{\overset{CH_3}{|}}{Si}}-O\right)_l + 2n(CH_3)NH$$

III to provide the carborane-siloxane polymer (III) wherein n has the same value as previously indicated.

As indicated, previously, and as is evident from the aforementioned equation, a wide variety of carborane disilanols can be employed in the preparation of the carborane-siloxane polymers. Illustrative disilanols include, among others, bis(hydroxydimethylsilyl)-m-carborane, bis(hydroxydimethylsilyl)-o-decacarborane, bis(hydroxydimethylsilyl)p-decacarborane, bis(hydroxydiethylsilyl)-m-decacarborane, bis(hydroxydiethylsilyl)-o-decacarborane, bis(hydroxydiethylsilyl)-p-decacarborane, bis(hydroxydipropylsilyl)-m-decacarborane, bis(hydroxydipropylsilyl)-o-decacarborane, bis(hydroxydipropylsilyl)p-decacarborane, bis(hydroxydibutyl silyl)-m-decacarborane, bis(hydroxydibutylsilyl)-o-decacarborane, bis(hydroxydibutylsilyl)-p-decacarborane, bis(hydroxydipentylsilyl)-m-decacarborane, bis(hydroxydipentylsilyl)-o-decacarborane, bis(hydroxydipentylsilyl)-p-decacarborane, bis(hydroxydiphenylsilyl)-o-decacarborane, bis(hydroxydiphenylsilyl)-p-decacarborane, bis(hydroxydiphenylsilyl)-m-decacarborane, bis(hydroxydiphenylchlorosilyl)-m-decacarborane, bis(hydroxydiphenylchlorosilyl)-o-decacarborane, bis(hydroxydiphenylchlorosilyl)-p-decacarborane and the like.

Illustrative bis silyl amines include, among others, bis(amino)silane, bis(amino)methylsilane, bis-(N-methylamino)methylsilane, bis(N,N-dimethylamino)-methylsilane, bis(N,N-dimethylamine)dimethylsilane, bis(N,N-dimethylamino-N',N'-diethylamino)dimethylsilane, bis(N-isopropylamino)methylsilane, bis(N,N-diisopropylamino)methylsilane, bis(N,N-diethylamino)-methylsilane, bis(N,N-dimethylamino-N'-methyl-N'-ethylamino)dimethylsilane, bis(N-isopropylamino-N'-ethylamino)dimethylsilane, bis(n-allylamino-N'-methylamino)dimethylsilane, bis(N,N-diallylamino)-dimethylsilane, bis(N,N-dimethylamino)methylvinylsilane, bis(N,N-diethylamino)ethylvinylsilane, bis(N,N-dimethylamino)phenylsilane, bis(N,N-dimethylamino)-methoxysilane, bis-(N,N-diethylamino)dimethoxysilane, bis(N-isopropylamino-N-allylamino)ethoxysilane, bis(N,N-dibutylamino)dimethylsilane, bis(N,N-dipentylamino)-dimetylsilane, (bis(N,N-methylamino)diphenylsilane, and the like.

In a second embodiment, the process comprises the steps of contacting disubstituted ureido-silanes or $\alpha,\omega$-ureido-siloxanes and carborane disilanols, in accordance with the following equation, to provide linear carborane-siloxane polymers having molecular weights of from about 5,000 up to about 150,000 and higher:

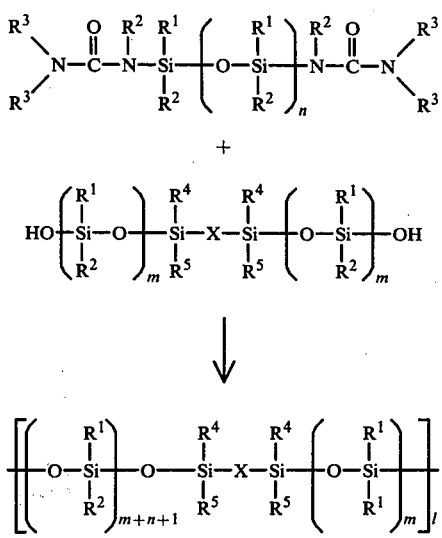

Wherein R, $R^1$-$R^5$, X, m, n and l are as previously indicated.

The following is a specific illustration of the condensation reaction involving carborane disilanol (I) and a ureido-silane (IV) to give the carborane-siloxane polymer III.

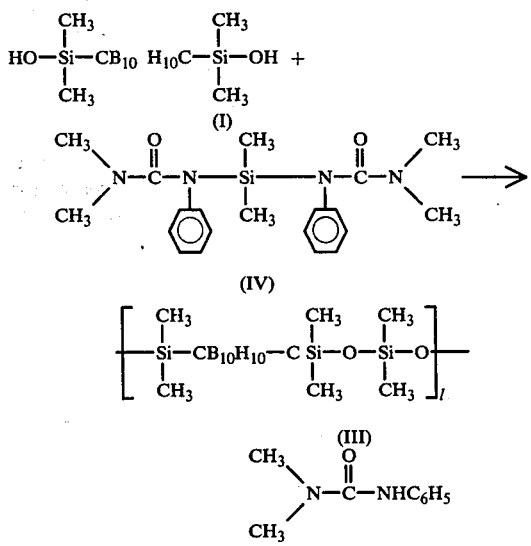

wherein l has the same value as previously indicated.

It has been observed that the use of ureido-silanes in place of silyl amines results in a polymeric product having a higher molecular weight. When carborane disilanol condensed with silyl diamine, dimethylamine is evolved. The evolved amine in some instances can cleave the carbon-silicone bond on the carborane disilanol to produce a polymer chain terminator. This prevents the formation of a high molecular weight polymer. In contrast the by-product of the ureido-silicanes are believed to be a less nucleophilic urea, which does not interfere with the formation of a high molecular weight product.

The reaction between ureido-silane and carborane disilanol is effected under relatively mild conditions and provides the polymer in excellent yields. In practice, the carborane-disilanol is merely added to the ureidosilane at room temperature in an inert atmosphere and stirred as the condensation reaction progresses. In some instances it may be desirable to promote the reaction by the application of heat.

As indicated above, the reaction is conducted in an inert atmosphere such as nitrogen and at atmospheric pressure. If desired the reaction can be conducted in an inert solvent such as chlorobenzene. However, in some instances the reactants themselves can serve as the reaction medium. In general, temperatures of from about −20° C. to about 200° C., and more preferably from about −10° C. to about 35° C. provide satisfactory results when a solvent is employed. In the absence of solvent, the reaction should be conducted above the melting point of the reaction mixture. The melt temperature depends on the reactant employed. For example, in the polymerization of 1,7 decacarborane disilanol with dimethylsilyl bis(N,N-dimethyl-N' phenylurea), the reaction was conducted between 70° C. and 160° C. in order to achieve maximum molecular weights.

Although the instant polymers contain the same recurring unit as in the Dexsil polymers, the latter, when polymerized in the presence of the ferric chloride catalyst results in a crosslinked polymer gum stock. In contrast, the silanol-ureido-silane polymerization of this invention results in a linear and soluble carborane-siloxane polymer with melting points of 68° and 90° C. as determined by Differential Scanning Calorimetry (DSC). The linear nature of these polymer gum stocks is demonstrated by their solubility in solvents such as methylene chloride, chlorobenzene and tetrahydrofuran and by results from gel permeation chromatography analysis. The proton magnetic resonance (pmr) indicated only two distinct $CH_3$—Si resonances (6 cps apart) with a ratio of 2/1 which corresponds to the expected structure.

A variety of ureido-silanes and α,ω- ureido-siloxanes can also be employed in the instant invention for the preparation of high molecular weight carborane-siloxane polymers. For example the ureido-silane and α,ω ureido-siloxanes can be characterized by the following generic formula:

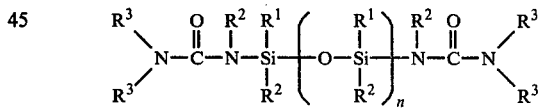

Wherein $R^1$-$R^3$ and n are as previously indicated.

Illustrative ureido-silanes include, among others, bis-(uredo)silane, bis(N,N'-dimethyluredio) methylsilane, bis(N,N-dimethyl-N'-methylureido)silane, bis(N,N-dimethyl-N'-methylureido)methylsilane, bis(N,N'-dimethylureido)dimethylsilane, bis(N,N'-diethylureido)-methylsilane, bis(N-methyl-N'-ethylureido)methylsilane, bis(N,N-dimethyl-N'-methylureido)dimethyl-silane, bis-(N,N'-diisopropylureido)methylsilane, bis(N-diisopropyl-N'-methylureido)methylsilane, bis(N,N'-diallyureido)-dimethylsilane, bis(N-alkyl-N'-methylureido)dimethylsilane, bis(N,-N'-dimethylureido)vinylsilane, bis(N,N'-diethylureido)-methylvinylsilane, bis(N,N-dipropylureido)ethylvinylsilane, bis(N,N'-dimethylureido)phenylsilane, bis(N,N-dimethylureidosilane, bis(N-methylureido)methoxysilane, bis(N-butylureido) dimethoxysilane, bis(N-pentylureido)-dimethylsilane, and the like.

In general, the ureido-silanes and α,ω ureido-siloxanes can be prepared by a variety of methods. For example, the reaction of silyl amine with phenyl isocyanate in ether provides the ureido-silane in accordance with the following equation:

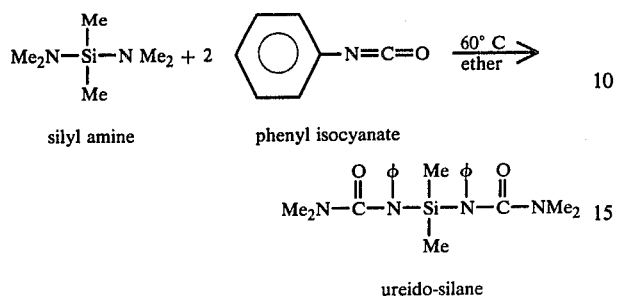

silyl amine        phenyl isocyanate ureido-silane

In a further embodiment, a silyl dicarbamate or α, ω -dicarbamoylsiloxanes is condensed with the carborane disilanols to provide linear carborane-siloxane polymers in accordance with the following equation:

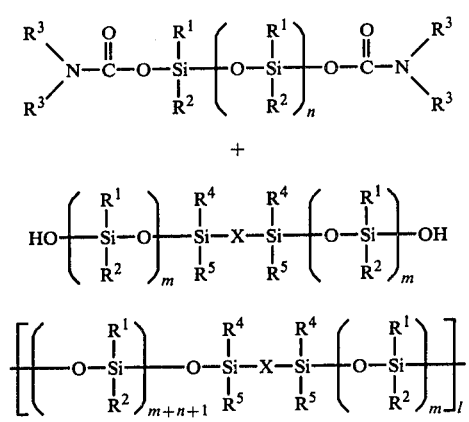

Wherein $R^1$-$R^5$, X, m, n and l are as previously indicated.

As in the case for the silyl urea and silyl amines a wide variety of silyl carbamates can be employed in the process of this invention. In general the silyl carbamates can be represented by the following generic formula:

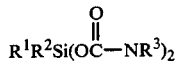

Wherein $R^1$-$R^3$ are as previously indicated. Illustrative silyl dicarbamates include, among others, bis(dimethylcarbamoyl)dimethylsilane, bis(diethylcarbamoyl) dimethylsiloxane, bis(diethylcarbamoyl) diethylsilane, bis(dipropylcarbamoyl)dimethylsilane, bis(dipropylcarbamoyl)diethylsilane, bis dibutylcarbamoyl) dimethylsilane, bis(N-methyl-N'-ethylcarbamoyl) dimethylsilane, bis(diethylcarbamoyl) vinylsilane, bis(dimethylcarbamoyl) methylvinylsilane, bis(dimethylcarbamoyl) dimethoxysilane, bis(diphenylcarbamoly) dimethylsilane, bis(dimethylcarbamoyl) diphenysilane, bis(dipentylcarbamoyl) dimethylsilane, bis(dibutylcarbamoyl) diethylsilane, bis(N,N-diethyl-N',N'-dimethylcarbamoyl) dimethylsilane, and the like.

Carborane-siloxane polymers containing higher weight portions of dimethylsiloxane moieties can also be prepared in accordance with the teachings disclosed in this invention. Thus, condensation of meta-decacarborane disilanol with $Me_2N$ $(Me_2 SiO)_4$ $Me_2Si$ $NMe_2$ under the usual reaction conditions will afford a gumstock with the following repeating unit:

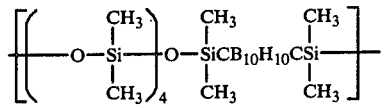

This illustrates the general extension of the disclosed technology to the synthesis of the class of polymers depicted below, wherein m has values of from 1-13, with 1-4 being preferred.

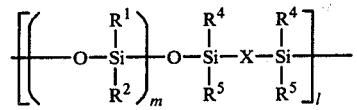

From the teachings of this invention it will be apparent to those skilled in the art that end functionalized oligomers are intermediates in the polymerization reaction. Oligomers have been successfully isolated and identified by nmr spectroscopy and through subsequent reactions. The oligomeric end functionalized products can contain either silanol end groups, silyl amine end groups, silyl urea end groups or silyl carbamate end groups. These products are valuable intermediates for the preparation of block and graft copolymers, RTV systems and the like.

If specifically desired, these oligomers can be prepared by appropriately adjusting the initial reaction stoichiometry as shown below:

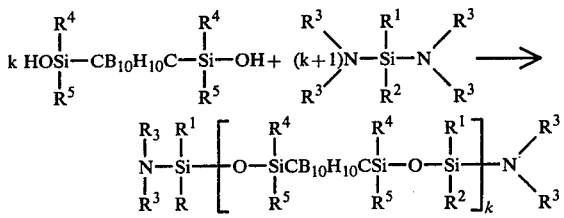

Wherein k has a value of from 1 to about 100.

Illustrative of a silanol end-capped prepolymers can be shown as follows:

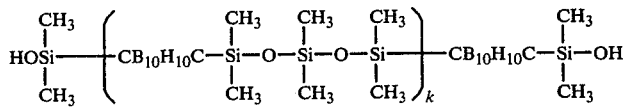

Wherein k has the same value as previously indicated. In a similar manner the prepolymers can be end-capped with silyl ureas.

In a further embodiment, the present invention is directed to curable gumstock compositions for use in the production of silicone elastomers and to the novel silicone elastomers derived from the gum compositions.

Silicone elastomers and methods for preparing such elastomers from heat-curable gumstock compositions which utilize as the gum compound, a diorganopolysiloxane gum containing vinyl siloxy units are well known in the art as witnessed, for example by U.S. Pat. Nos. 2,445,799; 2,954,357 and 3,183,205. Also, as previously indicated, more recent developments of silicone elastomers, have been directed to the carborane-siloxane products as set forth, for example, in U.S. Pat. Nos. 3,388,090; 3,388,091; 3,457,223; 3,463,801; 3,661,847 and the like.

The curable gumstock compositions of this invention can be comprised of carborane-siloxane homopolymers of copolymers, such as, block copolymers, random copolymers, and the like.

However, as indicated previously, the carborane-siloxane elastomers currently available have found only limited applications owing to fabrication difficulties and poor mechanical properties which are believed to be due to their crosslinked nature and low degree of polymerization.

In contrast, the carborane elastomers prepared by the process of the present invention can be fabricated with ease. Due to the essentially linear nature and high molecular weight of the polymers (gumstock) a wide latitude is available to impart the desired degree of crosslinking in the finished elastomer.

If desired, one can add a filler to heat curable gumstock composition to give substance and body to the crosslinked elastomer product. Any conventional filler heretofore employed in producing silicone rubbers can be used. Such fillers are also well known in the art. Illustrative examples of such conventional fillers are carbon black, silica base fillers such as pyrogenic silica, precipitated filler, fumed silica, silica gel, and the like, inorganic fillers such as diatomaceous earths, clay, calcium carbonate, titania, iron oxide, zinc oxide, aluminum oxide, and the like. Of course, the fillers can be employed individually or in combination with one another. Generally, it is preferred to employ finely divided silica base fillers of the highly reinforcing type either alone or in combination with inorganic fillers. The amount of filler, when used, that is present in the siloxane gumstock composition merely depends on the ultimate elastomer product desired. Generally amounts of filler from about 10 to about 200 parts by weight based on the wight of the siloxane gum employed will be sufficient for most purposes.

It should also be understood that the curable siloxane gumstock compositions, if desired, can contain other conventional silicone rubber additives which do not effect the invention or its basic purpose, such as pigments, dyestuffs, antioxidants, thermal stabilizers, oxide accelerators or retardants, and the like.

In a further embodiment, the present invention is directed to the preparation of carborane-siloxane elastomers which are characterized by markedly improved physical properties compared with commercially available silicone-containing elastomers. As previously indicated, the carborane-siloxane elastomers currently on the market are difficult to fabricate and have poor mechanical properties resulting from their crosslinked nature and low degree of polymerization. In contrast, the polymers of this invention can be reproducibly prepared with a minimum of difficulty and provide linear, carborane-siloxane polymers of relatively high molecular weights which can be converted to elastomers by conventional techniques.

In producing the carborane-siloxane elastomers one can employ any of the filler materials of the highly-reinforcing type consisting of inorganic compound, or any suitable combination of such filler materials, employed in the production of elastomers in accordance with heretofore customary procedures. It is possible to employ finely-divided silica-base fillers of the highly reinforcing type which are characterized by particle diameters of less than 500 millimicrons and by surface areas of greater than 50 square meters per gram. Inorganic filler materials of a composition, or of a particle diameter and surface area, other than those preferred, can be employed alone or in combination with the preferred fillers with good results. By way of illustration, such filler materials as titania, titanium dioxide, iron oxide, aluminum oxide, carbon black and the like, as well as those inorganic filler materials known as inert fillers which include, among others, diatomaceous earth, calcium carbonate and quartz are preferably employed in combination with highly-reinforcing silica fillers to lead substance or to body elastomers produced for those applications requiring only small amounts of a highly reinforcing silica filler.

The elastomers can be produced by blending or compounding a suitable starting carborane-siloxane polymer with a reinforcing filler on differential mixing rolls or in mixers, such as the Banbury Mixer, of the type employed in compounding organic rubber stock. The starting materials can be supplied to the mixing apparatus in any order, either all at once, or, when large amounts are to be compounded, they may be continually supplied to small increments.

One procedure for producing the elastomers is first to charge the carborane-siloxane polymer to the rolls of a milling apparatus or to a mixer and slowly adding the filler thereto. Adequate dispersion of the starting materials can be obtained by mixing or milling the ingredients for a period of from about eight or less to about twenty or more minutes.

Curing agents employed to cure the elastomeric compounds can be compounded with the polymer and filler at the same time or they may be added to the compounds immediately prior to curing operations. The latter method is preferred when a volatile organic peroxide is employed or is one which decomposes at relatively low temperatures.

The method for preparing the crosslinked carborane-siloxane elastomers of this invention is not critical and is based on the heretofore conventional procedures employed in curing i.e. crosslinking, a heat-curable gumstock composition. Said procedure is well known in the art and defined in any number of silicone rubber patents as shown for example by U.S. Pat. Nos. 2,445,799; 2,954,357 and 3,183,205. Briefly the preferred procedure involves adding a catalytic amount of any suitable conventional catalyst heretofore employed in producing such silicone rubber to the gum and heating the mixture at temperatures from about 230° F. to about 350° F. or above until the gum has been cured, i.e. crosslinked into a silicone elastomer. Of course the siloxane gum, and catalysts can be mixed in any manner or order. If a linear vinyl-containing siloxane copolymer fluid is employed, the amount of copolymer fluid can range from about 0.5 to about 5 parts by weight per 100 parts by weight of the crosslinkable vinyl containing diorganopolysiloxane gum used, while amounts of from about 0.5 to about 2.0 parts by weight per 100 parts by weight of gum will generally be sufficient for most purposes. It is also to be understood that the particular curing procedure is not critical and that any known method can be employed, such as light radiation curing of the gumstock composition, etc. Conventional precuring and/or post curing treatments can also be employed if desired.

As stated any conventional catalyst can be employed. Illustrative examples of such catalysts include the organic peroxide curing agents such as, di-t-butyl peroxide; t-butyl, triethylmethylperoxide; t-butyl-t-triptyl peroxide, dicumyl peroxide, benzoyl peroxide, t-butyl-perbenzoate, 1,4-dichlorobenzoyl peroxide; 2,4-dichlorobenzoyl peroxide, monochlorobenzoyl peroxide, and the like. Moreover, any single catalyst or mixtures of two or more different catalysts can be employed. Such curing agents are well known and described in the prior art.

The crosslinked carborane-siloxane elastomers of this invention have a wide range of utility including that which is well known in the art as shown for example by the above mentioned patents. For instance, the elastomers of this invention due to their properties are suited for use in the manufacture of air frame seals, gaskets, extrusions, e.g. wire coatings, and the like.

However, as indicated earlier, the polymers are particularly suited for applications where the elastomer must exhibit excellent high temperature and chemical stability. For example, seals, gaskets and the like comprised of the elastomers of this invention are useful for a variety of advanced aerospace, military and electronic applications.

The following examples are illustrative:

EXAMPLE 1

Preparation of Bis(hydroxydimethylsilyl)m - Carborane (I)

The meta-decacarborane disilanol (I) was prepared from the corresponding bis(chlorodimethylsilyl) m-decacarborane by adding to excess water. The disilanol was recrystallized twice from a boiling 10% solution in heptane solution in 75% overall yield, m.p. 99° C. (lit. 98°–99.5° C.)[2] In addition, a crude mixture of hydroxydimethylsilyl m- decacarboranes which was rich in the monohydroxydimethylsilyl-m-decacarborane was prepared from the crude monochloro compound for use in gas chromatographic analysis.
[2] H. K. Hall, J. Org. Chem. 29, 3539 (1964)

Analysis of the m- decacarborane disilanol was conducted as follows: to 0.05 g. m-decacarborane disilanol was added 0.25 ml bis(trimethylsilyl) acetamide (BSA) and a drop of trimethyl-chlorosilane and heated at 60° C. for 10 minutes. The analysis was carried out at 250° C. on a 2 meter ⅛" 10% S. E. 30/Teflon column at a flow of 30 cc/min. Retention times of ∼6 minutes and ∼16 minutes were obtained for the trimethylsilyl ethers of mono- and disilanol decacarboranes respectively. The twice recrystallized silanol had 99.5% di- and 0.5% monosilanol.

EXAMPLE 2

Preparation of Bis(N,N-dimethylamino)Dimethylsilane (II)

A solution of dimethyldichlorosilane in ether was sparged with an excess of dimethylamine at ambient temperatures. The filtration of the voluminous dimethylamine hydrochloride was carried out under anhydrous nitrogen. Ether was distilled off the filtrate and the silyl diamine was flash distilled. Redistillation on a 100 plate spinning band column yielded pure silyl diamine, b.p. 129° C. (lit. 128°–129° C.). Hydrolysis with an excess of aqueous hydrochloric acid in tetrahydrofuran and back titration with sodium hydroxide using bromcresol green, indicated that the silyl diamine was 99.5% pure. Analysis by VPC on SE-30 (100° C.) indicated a purity of >99.5%.

EXAMPLE 3

Neat Polymerization of Decacarborane Disilanol (I) and Silyl Diamine (II)

To a flame dried and silanized (using BSA reagent) 50 ml round bottom flask fitted with a magnetic stirring bar, nitrogen inlet, and reflux condenser was added 1.463 g. (10 mmole) silyl diamine (II) (sample was weighed into the flask in a dry box). When 2.928 g. (10 mmole) metadecacarborane-disilanol was added, the reaction mixture liquified rapidly with heat and dimethylamine evolution. The reaction temperature increased to ∼50° C. After 1 hour., the reaction contents solidified. Gradual heating with an oil bath to 86° C. over a 2 hour period resulted in just liquifying the solid. In 2 hours between 86°–98° C., a noticeable amount of white solid collected on the reflux condenser. Anhydrous methylene chloride was used (2 × 2 ml) to wash down the sublimate. The methylene chloride flashed off almost immediately. Dimethylamine evolution was still evident after 4 hours at ∼100° C. After 9 additional hours, no dimethylamine was detected. The reaction mixture was gradually heated to 190° C. at 40 mm to remove all volatiles and ensure complete reaction. The reduced viscosity R.V. (0.2 g/100 ml $CHCl_3$) at 25° C. was 0.055 dl/g. Gel permeation chromatography indicated a $M_W$ ∼2100. This material exhibited melting endotherms at 68° C. and 90° C. as determined by Differential Scanning Calorimetry (DSC).

EXAMPLE 4

Solution Polymerization of Decacarborane Disilanol (I) and Silyl Diamine (II)

To a 100 ml flame dried and silanized flask fitted with a magnetic stirring bar, nitrogen sparge tube, and refulx condenser was added 50 ml dry toluene (distilled over $P_2O_5$) and 3.057 g (10.45 mmole) decacarborane disilanol (I). About 30 ml of toluene was distilled off to ensure anhydrous conditions. The reaction mixture was cooled to room temperature and 1.528 g (10.45 mmole) of dimethylsilyldiamine containing 2 mole % vinylmethylsilyl diamine was added with 2 ml toluene. The reaction mixture was heated at ∼50° C. for 1 hour and the refluxed for 10 hours. The sample was coagulated in methanol and dried in a vacuum oven at 100° C. (50mm). The reduced viscosity in chloroform was 0.13 dl/g. Gel permeation chromatography indicated $\overline{M}_W$ = 6000, and vapor phase osmometry (VPO) in tetrahydrofuran gave a $\overline{M}_N$ = 4417. Proton magnetic resonance (A-60) in deuterated chloroform showed a low field and high field singlet (6cps apart) in the ratio of 2/1 respectively. The low field methyl groups are those on the silicone atom adjacent to the decacarborane group which exerts an electron withdrawing effect on the silicone groups.

Experiments similar to the above were run with the following variations:

1. Reaction mixture was heated to reflux immediately after the addition of silyl diamine. R.V. = 0.086 dl/g.
2. Same as above except 95% of theory of decacarborane disilanol was used. R.V. = 0.115 dl/g.
3. Same as above except 97% of theory of carborane disilanol was used. R.V. = 0.134 dl/g.

EXAMPLE 5

Preparation of Decacarborane-Siloxane Polymer by Sequential Addition of Silyl Diamine (II) to Carborane Disilano (I)

To a 100 ml flame dried silanized flask fitted with a magnetic stirring bar, nitrogen inlet, addition funnel, Dean Stark trap, and reflux condenser was added 2.591 g (8.86 mmole) decacarborane disilanol and 50 ml of anhydrous toluene. After the removal of 30 ml toluene, 1.440 g (9.84 mmoles) of silyl diamine (II) (10% excess) dissolved in 25 ml toluene was added dropwise into a refluxing solution of disilanol. In 35 minutes 33% of the silylamine was added. After an hour at reflux, the addition of silylamine was continued. In two hours a total of 80% of the silylamine was added, and the addition stopped again. No dimethylamine was evolving after one hour at reflux. The reaction mixture was refluxed overnight (10 ½ hours). The final 20% of the silylamine was diluted by distilling toluene in the reaction flask into the addition funnel. The addition was of the silylamine was carried out over a 13 hour period. An R.V. = 0.038 dl/g was obtained. The use of a 20% excess of silylamine added over a 20 hour period did not alter the results. The R.V. = 0.045 dl/g.

EXAMPLE 6

Preparation of Decacarborane-Siloxane Polymer by Sequential Addition of m- Decacarborane Disilanol (I) to Silyl Diamine (II)

To a flame dried silanized 100 ml flask fitted with a nitrogen sparge tube and reflux condenser was added 1.552 g (10.61 mmoles) silyl diamine and 20 ml anhydrous xylene (15 ppm water). The reaction mixture was brought up to reflux and 3.167 g (10.83 mmoles) decacarborane disilanol dissolved in 30 hot xylene was added dropwise (75%) over a 2 hour period. The last 25% was over another 2 hour interval. After refluxing 11 hours, the sample was coagulated in methanol. The R.V. = 0.087 dl/g (CHCl$_3$). The reaction was reapeated by adding 90% of the disilanol initially, and then 10% disilanol after 8 hours of reflux. The R.V. - 0.094 dl/g. Addition in sequences of 90%, 5%, and then 2% resulted in a R.V. = 0.091 dl/g.

EXAMPLE 7

Preparation of Decacarborane-Siloxane Polymer by the Low Temperature Addition of m-Decacarborane Disilanol (I) to Silyl Diamine (II) and Subsequent HYdrolysis To a flask was added 20 ml chlorobenzene and 1.827 g (12.48 mmoles) silyl diamine (10% excess) and the contents cooled to 10° C. A solution of 3.285 g (11.2 mmoles) of disilanol in 20 ml hot chlorobenzene was added dropwise over a 3 hour period. After the disilanol addition was complete, the reaction mixture was sparged with nitrogen between 10°-25° C. for 18 hours. At this point, some dimethylamine evolution was still detected. (A sample (5 ml) was removed for the hydrolysis reaction.) Another 24 hours at room temperature yielded a polymer, R.V. = 0.11 dl/g. The sample removed for hydrolysis (5 ml) and 2 ml THF were placed in a 10 ml erlenmeyer flask fitted with a magnetic stirring bar and cooled to ~0° C. with an ice bath. Approximately 20 μl of water (1 mmole) was added and the mixture was stirred at ice bath temperatures for several hours, and then at room temperature overnight. The reduced viscosity did not change (R.V. = 0.11 dl/g) from an additional 24 hours at room temperature, and an attempted hydrolysis reaction of the presumed silylamine end groups.

EXAMPLE 8

Preparation of Decacarborane-Siloxane Polymer from 50% meta- and 50% para-Decacarborane Disilanol Para-decacarborane disilanol was obtained from the para-carborane through a series of steps already described for the meta-isomer.

To a 100 ml flask was added 1.313 g (8.97) mmoles) silyl diamine (II) 20 ml chlorobenzene, and 1.312 g para- and 1.312 g meta-decacarborane disilanol (8.97 mmoles). The reaction mixture dissolved in several minutes at ambient temperatures. After 2 hours of stirring at ambient temperatures, the reaction mixture was heated to 100° C. in 2 hours. In 30 additional minutes, the reaction mixture was brought to reflux and heated for 10 hours. A sample was coagulated in methanol. The R.V. (CHCl$_3$) = 0.094 dl/g. Silyl diamine was then added incrementally to increase the molecular weight to R.V. = 0.190 d;/g. After each addition (~1 mole%), the reaction mixture was refluxed overnight. About 5 mole % of silylamine was added before any change in molecular weight was observed. Gel permeation chromatography in tetrahydrofuran indicated that the $\overline{M}_w$ = 16,800. The m-decacarborane-disilanol was used as a calibration factor. No crystalline melting point was observed for the resulting gum stock by DSC techniques.

EXAMPLE 9

Preparation of Decacarborane-Siloxane Polymer from 15% meta- and 85% para- Carborane Disilanol The reaction was essentially carried out as above. This decacarborane-siloxane was insoluble (0.2 g/100 ml) in chloroform at room temperature. The reduced viscosity in chlorobenzene at 100° C. was 0.17 dl/g. A determination of the R.V. of a meta-decacarborane siloxane sample in both chlorobenzene and chloroform at 25° C. indicated that the R.V. is 1.36 times higher in chloroform. Therefore, if all other factors are equal, the R.V. (CHCl$_3$) =0.23 dl/g. The resulting product showed a broad melting endotherm at 160°-200° C.

EXAMPLE 10

Preparation of Decacarborane -Siloxane Polymer from 70% meta- 30% para-Carborane-Disilanol To a flask with 1.338 g (9.14 mmoles) silyl diamine(II) (1% excess) and 20 ml chlorobenzene cooled to −10° C. was added 1.852 g meta- and 0.794 g para- decacarborane disilanol (9.05 mmoles). In 45 minutes at −10° to 0° C., all the decacarborane disilanol dissolves. The reaction mixture was kept at +10° C. for hours, 45 minutes at 15° C., and 14 hours at room temperature. At this time no dimethylamine was carried over by the nitrogen sparge. The reaction mixture was heated at 90° C. for 2 hours, and 130° for 2 more hours. Coagulation in methanol resulted in a sticky gummy material which was unlike the fine powder obtained in coagulation of other decacarborane-siloxane samples. Repeated dissolution and coagulation yield the same result. The R.V. = 0.104dl/g. About 1 mole % of silyl diamine was added at room temperature, and the reaction mixture stirred for 2 hours. At this time practically no dimethylamine evolution was observed. The reaction mixture was heated at reflux for 18 hours. The R.V. ($CHCl_3$) = 0.102dl/g. This material exhibited a weak melting endotherm at 47° C.

EXAMPLE 11

Preparation of Decarborane-Siloxane Polymer from 100% para-Decacarborane-Disilanol To 1.463 g (10 mmoles) of silyl diamine (II) (5% excess) and 20 ml xylene was added 2.873 g (9.5 mmoles) of para-decacarborane disilanol. Unlike the meta-decacarborane reaction, the para-silanol did not react at room temperature in xylene. The reaction mixture was heated in 1 hour to 128° C. before the solid liquified. After 20 hours in a 160° C. oil bath, the solvent had evaporated partially so that a white solid remained. The reduced viscosity at 100° C. in chlorobenzene was 0.25 dl/g. An extrapolated R. V. in chloroform is 0.34 dl/g. The melting point of this product was 220° C. (DSC).

EXAMPLE 12

Preparation of Decacarborane-Siloxane Polymer from 93% meta- 7% para- Decacarborane Disilanol In a manner similar to the previous examples, the reaction mixture was heated to reflux as soon as the components were added in stoichiometric amounts. Heat at reflux for 10 hours yielded, R.V.=0.091 dl/g ($CHCl_3$).

EXAMPLE 13

Preparation of Decacarborane-Siloxane Polymer from 6% Diphenyl - 94% Dimethyl meta- Decacarborane Disilanol (I)

In a manner similar to the previous examples a polymer was prepared from 7% diphenylsilyl bis(dimethyl amine) and 93% dimethylsilyl bis(dimethylamine) II and disilanol (I). The resulting polymer was characterized by R. V.=0.089 dl/g ($CHCl_3$). The polymer exhibited melting endotherms at 55° C. and 82° C. at (DSC).

EXAMPLE 14

Stability Studies of Decacarborane Disilanol Polymers

In order to evaluate the stability of carborane disilanol polymers the following test solutions were prepared:

(a) Dimethylamine in Chlorobenzene (DMA)

Approximately 1 g of dimethylamine (DMA) was sparged into 100 ml chlorobenzene. Tiration with 0.104 N $HClO_4$/acetic acid in acetic acid indicated a 0.25 M solution.

(b) Carbon Dioxide/Dimethylamine Solution ($CO_2$/DMA)

Sparging carbon dioxide (fritted disc) vigorously into 30 ml of the DMA/chlorobenzene for 15 minutes, yielded a solution (presumably the carbamic acid) which was 0.21 M by acid titration.

(c) Sulfur Dioxide/Dimethylamine Solution ($SO_2$/DMA)

The sulfur dioxide/dimethylamine solution was prepared in a similar manner as described above. Acid titration indicated a 0.19 M solution.

The procedure described was as follows:

To 0.050 g (0.17 mmoles) meta-decacarborane disilanol (II) in 0.25 ml chlorobenzene was added 0.25 ml BSA (bis-trimethylsilyl acetamide) and a drop of trimethyl chlorosilane. This control sample was compared with the DMA, DMA/$CO_2$, and DMA/$SO_2$ treated samples using vapor phase chromatographic techniques (VPC). To 0.050 g (0.17 mmoles) meta-decacarborane disilanol was added 0.25 ml of the DMA solution (0.16 mmole). The mixture was heated in a 50° C. oil bath with swirling for 5 minutes. The 0.25 ml of BSA and trimethylchlorosilane was added to convert the silanols to the ether. The same procedure was used for the DMA/$CO_2$ and DMA/$SO_2$ samples. VPC retention time for the monosilanol was 2.6 minutes and the disilanol, 6.9 minutes. The above test was repeated with allyl bromide (100% excess) in a dimethylamine/chlorobenzene solution (1.98 M). The disilanol was dissolved in the DMA/chlorobenzene solution and 0.25 ml allyl bromide added. The mixture was heated in a 50° C. bath for 5 minutes, converted to the ether, and analyzed.

The trimethylsilyl ethers of the silanols were analyzed on a 2 meter 10% fluorinated silicone on chromasorb G at 225° C. and 60 cc/min. flow.

The analysis indicated that the ratio of monosilanol ($HOSiMe_2CB_{10}H_{10}CH$) to disilanol increased from 0.38 percent/99.62 percent with the control to 12.3 percent/8.77 percent with the dimethylamine treated disilanol.

EXAMPLE 15

Allyl Bromide as a Dimethylamine Scavenger in Decacarborane

To a 100 ml flask fitted with a nitrogen sparge tube, magnetic stirrer, and reflux condenser was added 1.340 g (9.16 mmoles) silyl diamine (II), 15 ml chlorobenzene, 2.198 g (18.32 mmoles) allyl bromide(freshly distilled), and 2.679 g (9.16 mmoles) meta- carborane disilanol (I) at 25° C. Dimethylamine evolution was detected immediately. Unlike previous reactions, the disilanol was not completely in solution after 15 minutes and the reaction mixture was cloudy. The precipitate may also be the ammonium salt from dimethylamine and allyl bromide. In 15 additional minutes, it appeared that the disilanol was forming a gum. A 45°–58° bath was used to attempt to facilitate the solution process. However, after 1 hour, the solid did not dissolve. Increasing the temperature to 82° results in the dissolution of the solid, and two liquid layers are formed indicating that the solid was the ammonium salt. After 23 hours at 87°, 2 ml of the top layer of the reaction mixture was coagulated in 20 ml methanol. Yield 0.50 g. R.V. ($CHCl_3$)=0.094 dl/g.

EXAMPLE 16

Allyl Bromide as a Dimethylamine Scavenger in Low Temperature Decacarborane Siloxane Polymerization To a 100 ml flask was added 1.354 g (9.256 mmoles) silyl diamine (II) and 15 ml chlorobenzene, and the mixture was cooled to −10° C. Then 2.708 g (9.256 mmoles) of meta- decacarborane disilanol (I) was added. Most of the silanol does not dissolve. In 10 minutes the bath temperature was increased to 0° C. In 40 minutes, all the silanol dissolved. The reaction mixture was cooled to −10° C. and ~1.6ml (18.5 mmoles) allyl bromide was added rapidly. Warming the bath to 10° C. in 10 minutes resulted in the rapid evolution of dimethylamine. After 45 minutes at 10° C., the DMA evolution was still quite strong. Increasing the temperature to 18° C. (45 minutes) resulted in a cloudy solution which probably indicates the formation of the ammonium salt of allyl bromide. The reaction mixture was stirred at 25° C. for 25 hours. No amine evolution was detected with a wet pH paper. R.V. ($CHCl_3$)=0.086 dl/g.

EXAMPLE 17

Preparation of Decacarborane -Siloxane Polymer from meta-Decacarborane Disilanol(I) and Silyl Urea To a flame dried 3-necked 100 ml. flask fitted with a magnetic stirring bar, thermometer, nitrogen inlet, dean stark trap, and reflux condenser was added ~1.7 ml; 1.5000g. (10.252 mmoles) silyl diamine (II) and 20ml. anhydrous chlorobenzene. The 2.440g. of phenyl isocyanate was added, and the transfer completed with 5 ml. of chlorobenzene. The reaction mixture was carefully heated to 60° C. and kept at 60° C. for 30 minutes. The reaction mixture was cooled to room temperature and 2.9991g. m-carborane disilanol was added to the reaction mixture and stirred at room temperature. No rapid reaction was evidenced by an exotherm on the dissolution of silanol was observed until 50° C. The temperature was gradually increased to 100° C. over several hours and maintained at 100° C. overnight. Additional heating at approximately 130° C. for several hours there was no apparent change except that some of the solvent evaporated and the mixture appears slightly more viscous. Upon cooling a white precipitate appeared which has the consistency of soft wax. A small amount of precipitate was dissolved in chlorobenzene, filtered to remove by-product urea and coagulated in 40 ml methanol. The leading polymeric product had an RV=0.139 dl/g. Further heating of the mixture for several hours at temperatures up to 180° C. and separating and coagulating as above gave a carborane-siloxane polymeric product having RV=0.138 dl/g.

EXAMPLE 18

Preparation of Decacarborane-Siloxane Polymers from Silyl Carbamates

(a) Solution Polymerization in Chlorobenzene

To a flame dried 3-necked 100 ml round bottom flask equipped with a condenser, magnetic stirring bar, nitrogen inlet, and thermometer was added 2.3259 g (9.927 mmoles) of bis (N,N-dimethylcarbamoyl) dimethyl silane 2.9374 g (10.042 mmoles) bis (hydroxydimethylsilyl)-m-decacarborane, and 20 ml of anhydrous chlorobenzene with stirring. The reaction was rapid as indicated by the immediate dissolution of the relatively insoluble silanol. Accompanying the polymerization was the simultaneous evolution of dimethylamine. After stirring for 22 hours at room temperature and heating for 2 hours at reflux, the sample was coagulated in methanol. The resulting cloudy solution did not yield any polymer on filtration indicating molecular weights of less than R.V. of 0.05 dl/g. Polymerizations at 99/100 and 102/100, molar ratios of silyl carbamate to silanol ratios yielded similar molecular weights as approximated by their solubility in methanol.

(b) Low Temperature Vacuum Polymerization in Chlorobenzene

Titration of a sample of the same silyl carbamate employed above in tetrahydrofuran/acetic acid with perchloric acid indicated a purity of 93.5±1%. The assumption was made that the impurity was dimethylsiloxane obtained from the hydrolysis of the silyl carbamate. To a 100 ml 3-necked flask fitted with a nitrogen inlet, thermometer, condenser, magnetic stirring bar, and vacuum outlet was added 2.4780 g (10.576 mmoles) of the silyl carbamate and 10 ml of chlorobenzene. The mixture was cooled to ~4° C. with an ice bath, 2.9560 g (10.106 mmoles) of the decacarborane disilanol added and house vacuum (~60 mm) applied. Within 3 minutes, all the silanol had reacted. In 18 minutes the ice bath was removed, and the contents were allowed to come to room temperature. After stirring for 10 hours under vacuum, some dimethylamine was still detected in the nitrogen effluent. Coagulation in methanol indicated an R.V. <0.05 dl/g based on the polymer's solubility in methanol.

(c) Solution Polymerization in Heptane

To a 100 ml flask fitted with a nitrogen inlet and a magnetic stirring bar was added 2.9087 (9.944 mmoles) of the decacarborane disilanol, 2.4525 g (10.467 mmoles) of the silyl carbamate, and 10 ml of heptane. Dimethylamine evolution started immediately, however, the silyl carbamate took 13 minutes to dissolve completely while the silanol dissolved in 40 minutes at room temperature. Within 4 hours the polymer precipitated from solution and no dimethylamine evolution was noted. More heptane was added (20 ml), but the polymer did not dissolve. This mixture was heated to re-dissolve the polymer and the solution refluxed for 3 hours. Only a trace of dimethylamine was noted. Coagulation in methanol yielded a polymer with R.V.=0.06 dl/g.

(d) Neat Polymerization

To a 100 flask under nitrogen was added 2.886 g (9.855 mmoles) decacarborane disilanol and 2.3122 g (9.868 mmoles) silyl carbamate (nmr pure). After 2 minutes at 40° C., dimethyl amine evolution was noted. In 7 minutes, stirring was started. A light amount of dimethylamine was still detected in the nitrogen effluent. In 2½ more hours, no dimethylamine was detected from this easily stirred liquid. After stirring overnight at 40°, isolation by coagulation yielded a polymer of R.V.=0.042 dl/g.

EXAMPLE 19

D5-Decacarborane Dimethylsiloxane Polymer m-Decacarborane disilanol (I) and an equivalent amount of $Me_2N(Me_2SiO)_4 Me_2SiNMe_2$ are reacted at room temperature. The resulting gummy polymeric product has a molecular weight (Mw) of about 10,500. Infrared analysis shows bands characteristic of BH, $CH_3$-Si, Si-O, and carborane cage linkages. Thermo gravimetric analysis (TGA) shows gradual weight loss from 400°–600° C. and sharp weight loss from 600°–640° C.

Although the invention has been illustrated by the preceding examples it is not to be construed as being limited to the materials employed therein, but rather, the invention relates to the generic area as hereinbefore disclosed. Various modifications and embodiments can be made without departing from the spirit and scope thereof.

What is claimed is:

1. A process for the preparation of a carborane-siloxane composition comprised of at least one essentially liner carborane-siloxane polymer having the following formula:

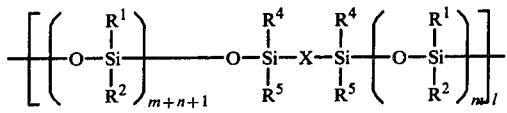

which process comprises the steps of:
(a) contacting under an inert atmosphere a carborane disilanol of the formula:

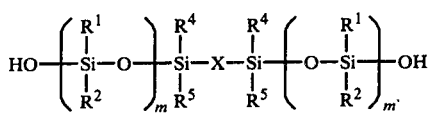

with a silicone compound selected from the group consisting of:
(i) ureido-silanes or , ω-ureido-siloxanes of the formula:

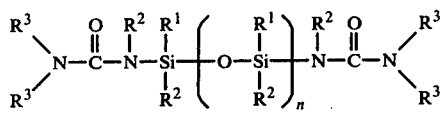

pr
(ii) silyl carbamates or α, ω-carbamoyl-siloxanes of the formula:

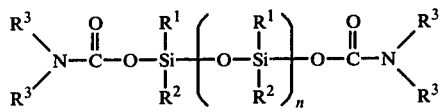

wherein:
(1) $R^1$ and $R^2$ individually represent hydrogen, or groups containing up to 14 carbon atoms and selected from the group consisting of alkyl, alkenyl, cycloalkyl, aryl, alkaryl, aralkyl, alkoxy, alkoxyaryl, cyanoalkyl, morpholinyl, and pyridinyl;
(2) $R^3$ individually represents hydrogen or a group containing up to 14 carbon atoms and selected from the group consisting of alkyl, alkenyl, cycloalkyl, alkaryl, aralkyl, alkoxyaryl, haloaryl, cyanoalkyl, morpholinyl and pyridinyl; and wherein 2 $R^3$s, can when taken together contain up to 6 carbon atoms and represent alkylene, dialkylene amine or alkyl-substituted dialkylene amine;
(3) $R^4$ and $R^5$ individually represent hydrogen or groups containing up to 14 carbon atoms and selected from the group consisting of alkyl, alkenyl, aryl, alkaryl, alkoxy and alkoxyalkyl,
(4) X represents a divalent radical derived from 1,7-decacarborane, 1,12 -decacarborane, 1,10-octacarborane, 1,6-octacarborane, 2,4-pentacarborane, 1,6-tatracarborane, 9-alkyl-1,7-decacarborane, 9,10-dialkyl-1,7-decacarborane, 2-alkyl-1,12-decacarborane, 2-alkyl-1,10-octacarborane, 8-alkyl-1,6-octacarborane, decachloro-1,7decacarbornae, decachloro-1,12-decacarborane, octachloro-1,10-octacarborane, decafluoro-1,7-decacarborane, decafluoro-1,12- decacarborane, octafluoro-1,10-octacarborane, or mixtures thereof,
(5) m and N individually have a value of from 0 to 4 and l has a value such that the molecular weight of the polymer is up to about 150,000 and higher; and
(b) recovering said carborane-siloxane polymer.

2. The process of claim 1 wherein said silicone compound is said ureido-silane or α,ω-ureido-siloxane.

3. The process of claim 1 wherein said silicone compound is said silyl carbamate or α, ω-carbamoyl siloxane.

4. The process of claim 1 wherein said carborane disilanol is bis(hydroxydimethylsilyl)meta-carborane.

5. The process of claim 4 wherein said ureido-silane is bis(N,N-dimethylureido)dimethylsilane.

6. The process of claim 4 wherein said silyl carbamate is bis(N,N-dimethylcarbamoyl) dimethylsilane.

7. A carborane-siloxane composition comprised of at least one essentially linear carborane-siloxane polymer having the recurring unit of claim 1 wherein m and n are zero.

8. The composition as defined in claim 7 wherein at least one carborane-siloxane polymer contains at least one methyl siloxy group.

9. The composition as defined in claim 7 wherein at least one carborane-siloxane polymer contains at least one vinyl group.

10. The composition as defined in claim 7 wherein at least one carborane-siloxane polymer contains at least one vinyl siloxy group.

11. The composition as defined in claim 7 wherein at least one carborane-siloxane polymer contains at least one phenyl group.

12. The composition as defined in claim 7 wherein X is an octacarboranyl group.

13. The composition as defined in claim 7 wherein X is a 2,4-pentacarboranyl group.

14. The composition as defined in claim 7 wherein X represents a decacarboranyl group.

15. The cross-linked carborane-siloxane elastomer product derived from heat curing a composition as defined in claim 9.

16. The cross-linked carborane-siloxane elastomer product derived from heat curing a composition as defined in claim 10.

17. The cross-linked carborane-siloxane elastomer product derived from heat curing a composition as defined in claim 12.

18. The cross-linked carborane-siloxane elastomer product derived from heat curing a composition as defined in claim 14.

* * * * *

UNITED STATES PATENT OFFICE
CERTIFICATE OF CORRECTION

Patent No. 4,145,504　　　　　　　　Dated March 20, 1979

Inventor(s) E. N. Hedaya et al.

It is certified that error appears in the above-identified patent and that said Letters Patent are hereby corrected as shown below:

In claim 1, paragraph (a)(i), after the formula;

"pr" should read "or"

In claim 1, paragraph (a)(ii) (5), line 1;

"N" should read "n".

Signed and Sealed this

Twenty-ninth Day of May 1979

[SEAL]

Attest:

RUTH C. MASON
*Attesting Officer*

DONALD W. BANNER
*Commissioner of Patents and Trademarks*